(12) United States Patent
May (10) Patent No.: US 11,439,438 B2
(45) Date of Patent: Sep. 13, 2022

(54) SPINAL IMPLANT SYSTEM AND METHODS OF USE

(71) Applicant: WARSAW ORTHOPEDIC INC., Warsaw, IN (US)

(72) Inventor: Jason M. May, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 65 days.

(21) Appl. No.: 17/063,979

(22) Filed: Oct. 6, 2020

(65) Prior Publication Data
US 2021/0015522 A1 Jan. 21, 2021

Related U.S. Application Data

(62) Division of application No. 15/404,196, filed on Jan. 12, 2017, now Pat. No. 10,835,271.

(51) Int. Cl.
*A61B 17/70* (2006.01)

(52) U.S. Cl.
CPC .......... *A61B 17/7037* (2013.01); *A61B 17/70* (2013.01); *A61B 17/7035* (2013.01)

(58) Field of Classification Search
CPC ................. A61B 17/70; A61B 17/7032–7038
See application file for complete search history.

(56) References Cited

U.S. PATENT DOCUMENTS

| | | | |
|---|---|---|---|
| 5,885,286 A | 3/1999 | Sherman et al. | |
| 6,565,566 B1 | 5/2003 | Wagner et al. | |
| 8,034,089 B2 | 10/2011 | Matthis et al. | |
| 8,097,025 B2 | 1/2012 | Hawkes et al. | |
| 8,167,910 B2 | 5/2012 | Nilsson | |
| 8,197,518 B2 | 6/2012 | Hammill, Sr. et al. | |
| 8,298,265 B2 | 10/2012 | Purcell et al. | |
| 8,298,275 B2 | 10/2012 | Rezach et al. | |
| 11,090,087 B2* | 8/2021 | Spangler | A61B 17/7082 |
| 2004/0098933 A1* | 5/2004 | Bourque | B60J 1/00 52/204.5 |
| 2007/0270839 A1 | 11/2007 | Jeon et al. | |
| 2011/0093021 A1 | 4/2011 | Fanger et al. | |
| 2013/0103098 A1* | 4/2013 | Jackson | A61B 17/8605 606/305 |
| 2015/0142059 A1* | 5/2015 | Biedermann | A61B 17/7037 606/266 |
| 2019/0150989 A1* | 5/2019 | Biester | A61B 17/863 |

* cited by examiner

*Primary Examiner* — Tessa M Matthews
(74) *Attorney, Agent, or Firm* — Sorell, Lenna & Schmidt, LLP (57) ABSTRACT

A method of assembly for a bone fastener is provided. The method includes the steps of: engaging a retainer with an implant receiver in a relatively fixed position; translating the retainer relative to the implant receiver to an expandable orientation; and manually engaging a screw shaft with the retainer to connect the implant receiver with the screw shaft. Implants, systems and instruments are disclosed.

20 Claims, 6 Drawing Sheets

SPINAL IMPLANT SYSTEM AND METHODS OF USE

CROSS-REFERENCE TO RELATED APPLICATION

This application is a divisional of U.S. patent application Ser. No. 15/404,196, filed Jan. 12, 2017, which is expressly incorporated herein by reference, in its entirety.

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a method of assembly for a bone fastener is provided. The method includes the steps of: engaging a retainer with an implant receiver in a relatively fixed position; translating the retainer relative to the implant receiver to an expandable orientation; and manually engaging a screw shaft with the retainer to connect the implant receiver with the screw shaft. In some embodiments, implants, systems and instruments are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly; in terms of a spinal implant system including a bone fastener. In some embodiments, the spinal implant system includes an implant comprising a bone fastener, such as, for example, a pedicle bone screw.

In some embodiments, the spinal implant system comprises a head assembly including a part, such as, for example, a crown and a retainer that is pre-assembled with an implant receiver. In some embodiments, the retainer facilitates attachment of an implant receiver with a screw shaft in a robust connection. In some embodiments, the spinal implant system comprises a modular screw system including screw shaft assemblies and implant receiver/head assemblies that may be joined together during manufacturing or intra-operatively, such as, for example, during a surgical procedure in an operating room.

In some embodiments, the spinal implant system comprises a bone fastener including a head assembly having a head, a crown and a collet; and a screw shaft assembly having a screw shaft. In some embodiments, the bone fastener is employed with a method of assembly that includes the step disposing the collet in a closed position with one or more components of the head assembly. In some embodiments, the collet is engaged with the one or more components of the head assembly with sufficient torque to prevent disassembly such that the collet is locked in the closed position with the head assembly. In some embodiments, prior to connection of the screw shaft with the head assembly, the method includes the step of rotating the collet, for example, 180 angular degrees, relative to the one or more components of the head assembly to an open position. In some embodiments, the method includes the step of connecting the screw shaft with the collet in the open position. In some embodiments, subsequent to connecting the screw shaft with the collet, the method includes the step of disposing the collet in the closed position with the head assembly. In some embodiments, the collet is rotated, for example, 180 angular degrees, relative to one or more components of the head assembly to the closed position.

In some embodiments, the crown includes a drive feature engageable with a surgical instrument from a top surface of the head assembly. In some embodiments, the crown includes one or more driving members engageable with the collet. In some embodiments, the one or more driving members are engageable with a surgical instrument to rotate the crown. In some embodiments, the collet includes one or more receiving notches that engage the one or more driving members of the crown for rotation of the collet. In some embodiments, the collet includes one or more slots that allow a head of a screw shaft to snap into engagement with the collet.

In some embodiments, a head of the screw shaft component may be assembled to the retainer using a force and/or interference fit. In some embodiments, the retainer is expandable between a capture orientation with the head of the screw shaft and an expanded orientation. In some embodiments, a head assembly includes a crown, a retainer and a tulip. In some embodiments, a method includes the step of engaging the screw shaft assembly with the head assembly such that the retainer captures the head of the screw shaft and is disposed with the implant receiver in a closed position to create a permanent assembly of a bone fastener.

In some embodiments, the spinal implant system comprises a modular system that includes a bone fastener including an array of members, such as, for example, bone screw shafts that can be selectively coupled to members, such as, for example, receivers. In some embodiments, the spinal implant system comprises a selectively coupled bone fastener that can be assembled on a surgical table or in-situ. In some embodiments, the selectively coupled bone fastener is assembled with a force of less than 50 Newtons (N). In some embodiments, the bone fastener assembly comprises manually engaging the screw shaft in a pop-on engagement with the head/receiver of the bone fastener. In some embodiments, a force required to manually engage a screw shaft with a head/receiver of the bone fastener is in a range of 2 to 50 N. In some embodiments, a force required to manually engage a screw shaft with a head/receiver of the bone fastener is in a range of 5 to 10 N. In some embodiments, a screw shaft is manually engaged with a head/receiver of the bone fastener, as described herein, such that removal of the head/receiver from the screw shaft requires a force and/or a pull-out strength of at least 5000 N.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims; "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure, Alternate embodiments are disclosed. Reference is made in detail to the exemplary embodiments of the present disclosure; which are illustrated in the accompanying figures. Turning to FIGS. 1-12, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 180. Bone fastener 180 comprises a member, such as, for example, a screw shaft 12 and a head assembly 13. In some embodiments, screw shaft 12 and head assembly 13 are assembled in situ or prior to implant to form bone fastener 180, as described herein.

Head assembly 13 includes a member, such as, for example, a receiver 14. Receiver 14 extends along and defines an axis X1. Receiver 14 includes a pair of spaced apart arms 16, 18 that define an implant cavity 20 therebetween configured for disposal of a component of a spinal construct, such as, for example, a spinal rod (not shown).

Arms 16, 18 each extend parallel to axis X1. In some embodiments, arm 16 and/or arm 18 may be disposed at alternate orientations, relative to axis X1 such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone fastener 180. In some embodiments, arms 16, 18 are connected at proximal and distal ends thereof such that receiver 14 defines a closed spinal rod slot.

Cavity 20 is substantially U-shaped. In some embodiments, all or only a portion of cavity 20 may have alternate cross section configurations, such as, for example, closed, V-shaped, W-shaped, oval, oblong triangular, square, polygonal, irregular, uniform, non-uniform, offset, staggered, and/or tapered. Receiver 14 includes an inner surface 22. A portion of surface 22 includes a thread form 24 located adjacent arm 16 and a thread form 26 located adjacent arm 18. Thread forms 24, 26 are each configured for engagement with a coupling member, such as, for example, a setscrew (not shown), to retain the spinal rod within cavity 20. In some embodiments, surface 22 may be disposed with the coupling member in alternate fixation configurations, such as, for example, friction fit, pressure fit, locking protrusion/recess, locking keyway and/or adhesive. In some embodiments, all or only a portion of surface 22 may have alternate surface configurations to enhance engagement with the spinal rod and/or the setscrew, such as, for example, rough, arcuate, undulating, mesh, porous, semi-porous, dimpled and/or textured. In some embodiments, receiver 14 may include alternate configurations, such as, for example, closed, open and/or side access.

Receiver 14 includes a surface 40. Surface 40 defines a channel 42. Channel 42 is configured for disposal of a part, such as, for example, a crown 44, as described herein. In some embodiments, channel 42 is separated from surface 22 by a protrusion, such as, for example, a lip 48. In some embodiments, lip 48 is configured as a stop surface to limit translation of crown 44. In some embodiments, all or only a portion of surfaces 30, 40 may have alternate surface configurations, such as, for example, rough, arcuate, undulating, mesh, porous, semi-porous, dimpled and/or textured.

Receiver 14 includes a surface 50. Surface 50 includes a threaded surface 52. In some embodiments, surface 52 may include a single thread turn or a plurality of discrete threads. Surface 52 is configured for a threaded engagement with a surface of a retainer, such as, for example, a collet 90, as described herein. Engagement of surface 52 with a surface of collet 90 is configured to translate collet 90 between a releasable, relatively fixed position, an open position for engaging and connecting with screw shaft 12 and a closed position to fix position of collet 90 and/or screw shaft 12 with receiver 14, and/or assemble the components of bone fastener 180 in a fixed connection, as described herein. In some embodiments, bone fastener 180 may be assembled for permanent assembly and/or an assembled configuration that may be revised.

Crown 44 is configured for disposal within cavity 20 and channel 42. Crown 44 includes a wall 66 having an end surface 68 and an end surface 70. Surface 68 is configured to define at least a portion of cavity 20. Surface 70 defines an engagement portion 78 configured for engagement with a head 120 of screw shaft 12, as described herein. In some embodiments, engagement portion 78 includes a concave configuration to facilitate engagement with head 120.

Wall 66 includes a surface 72 and a surface 74. Surface 72 defines a circular opening. In some embodiments, all or only a portion of surface 72 may have alternate cross section configurations, such as, for example, oval, oblong triangular, square, polygonal, irregular, uniform, non-uniform, offset, staggered, and/or tapered.

Surface 72 defines a plurality of mating elements, such as, for example, recesses 76. In some embodiments, surface 72 includes one or a plurality of recesses 76 disposed circumferentially about surface 72. In some embodiments, recesses 76 include a concave configuration. Recesses 76 are configured for a mating engagement with a surgical instrument such as a driver. Engagement with the surgical instrument facilitates rotating crown 44 and collet 90 connected therewith for translation of collett 90 between the relatively fixed, open and closed positions, as described herein. In some embodiments, recesses 76 may have various cross-section configurations, such as, for example, oval, oblong, triangular, rectangular, square, polygonal, irregular, uniform, non-uniform, variable, tubular and/or tapered. In some embodiments, recesses 76 may have various surface configurations, such as, for example, smooth and/or surface configurations to enhance engagement with the surgical instrument, such as, for example, rough, arcuate, undulating, porous, semi-porous, dimpled, polished and/or textured.

Surface 74 defines a plurality of mating elements, such as, for example, flanges 80 extending therefrom. In some embodiments, flange 80 extends substantially perpendicular to axis X1 In some embodiments, flange 80 may be disposed in various orientations, such as, for example, transverse and/or at angular orientations, such as acute or obtuse relative to axis X1.

In some embodiments, surface 74 includes one or a plurality of flanges 80 disposed circumferentially in a spaced apart relation about surface 74. In some embodiments, flanges 80 include a convex configuration. In some embodiments, all or only a portion of flanges 80 may have alternate configurations, such as, for example, oval, oblong, triangular, square, polygonal, irregular, uniform, non-uniform, offset, staggered, and/or tapered.

Flanges 80 are configured for a mating engagement with collet 90, as described herein. Flanges 80 engage a surface of collet 90 to simultaneously rotate collet 90 to drive and translate crown 44 and collet 90. In some embodiments, collet 90 is rotated 180 degrees to translate collet 90 between the open and closed positions, as described herein.

Collet 90 includes a wall, such as, for example, a circumferential sleeve 92. Sleeve 92 includes an end surface 94 and an end surface 96. Sleeve 92 includes a surface 98 and a surface 100. Surface 94 defines a circular opening configured for disposal of head 120. In some embodiments, all or only a portion of surface 94 may have alternate cross section configurations, such as, for example, oval, oblong triangular, square, polygonal, irregular, uniform, non-uniform, offset, staggered, and/or tapered.

Surface 94 defines a plurality of mating elements, such as, for example, notches 102. In some embodiments, surface 94 includes one or a plurality of notches 102 disposed circumferentially about surface 94. In some embodiments, notches 102 include a concave configuration. In some embodiments, all or only a portion of notches 102 may have alternate configurations, such as, for example, oval, oblong, triangular, square, polygonal, irregular, uniform, non-uniform, offset, staggered, and/or tapered. Notches 102 matingly engage flanges 80. Engagement of flanges 80 with notches 102 connects crown 44 and collet 90 such that crown 44 drives and rotates collet 90 to translate collet 90 between an open position for engaging and connecting with screw shaft 12 and a closed position to fix position of collet 90 and/or screw shaft 12 with receiver 14, as described herein. In some embodiments, collet 90 can be mated with crown 44 in various configurations, such as, for example, threaded connection, clips, dovetail connection, key/keyslot, friction fit, pressure fit, interlocking engagement, dovetail connection, hook and loop closure, clips, barbs, tongue in groove, threaded, magnetic, key/keyslot, drill chuck and/or adhesive.

Sleeve 92 includes a surface that defines gaps, such as, for example, a plurality of spaced apart slots 108 that extend through the wall of sleeve 92. Slots 108 extend along a portion of sleeve 92 and are disposed circumferentially about sleeve 92. Slots 108 provide flexibility to sleeve 92 and are configured to facilitate expansion and/or contraction of collet 90, as described herein. In some embodiments, sleeve 92 can include one or a plurality of slots 108. In some embodiments, one or more slots 108 may have alternate configurations, such as, for example, irregular, uniform, non-uniform, offset, staggered, and/or tapered.

Figure 1:
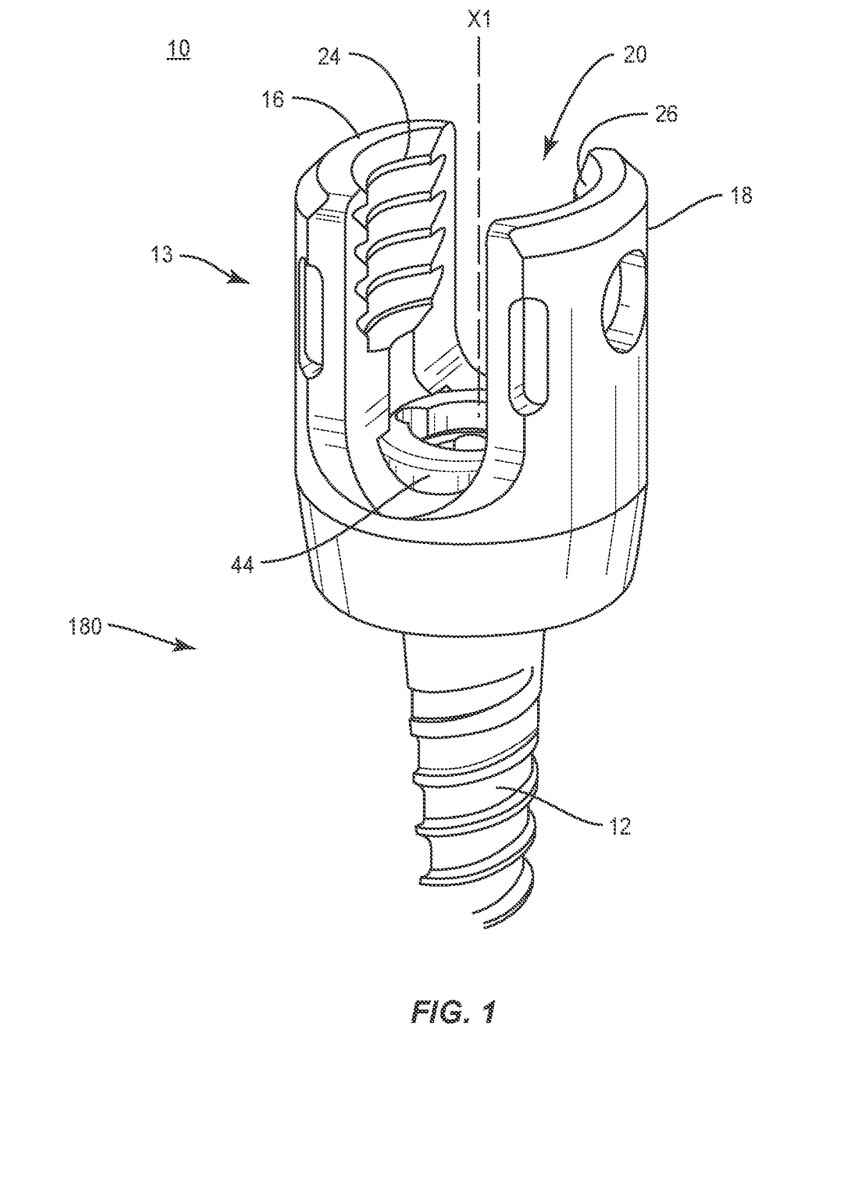
FIG. 1 is a perspective view of components of one embodiment of a spinal implant system in accordance with the principles of the present disclosure.
Figure 2:
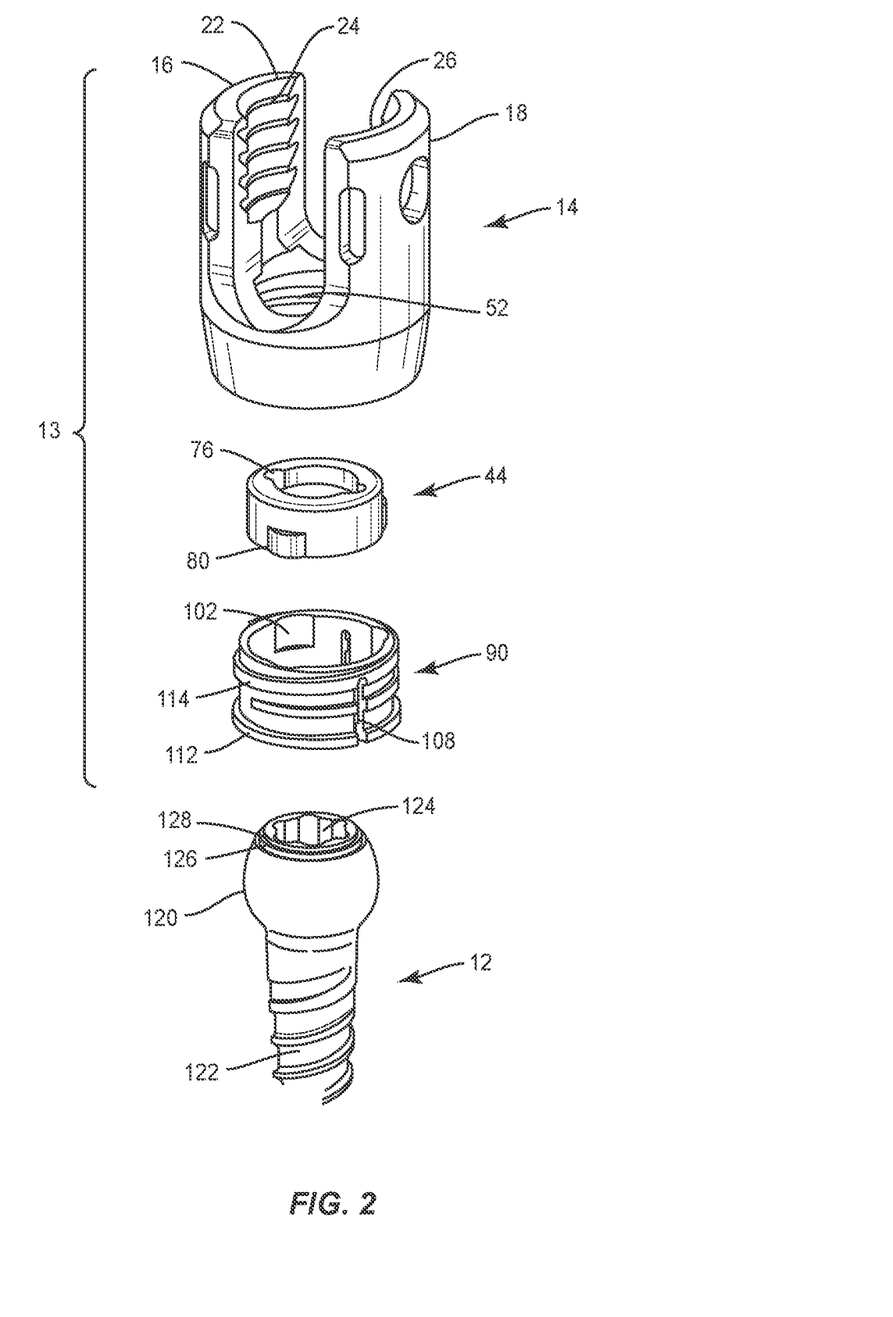
FIG. 2 is a perspective view of the components shown in FIG. 1 with parts separated.
Figure 3:
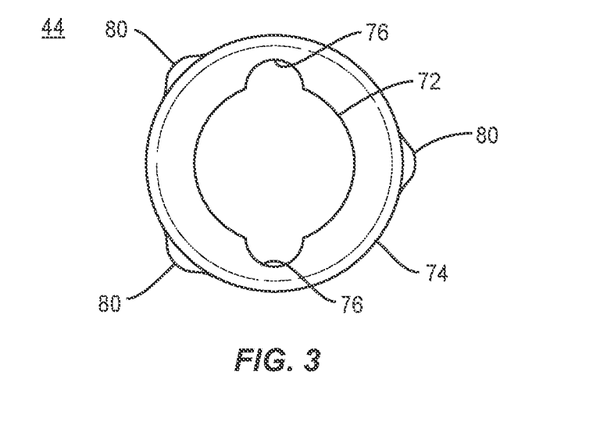
FIG. 3 is a plan view of components of the system shown in FIG.
Figure 4:
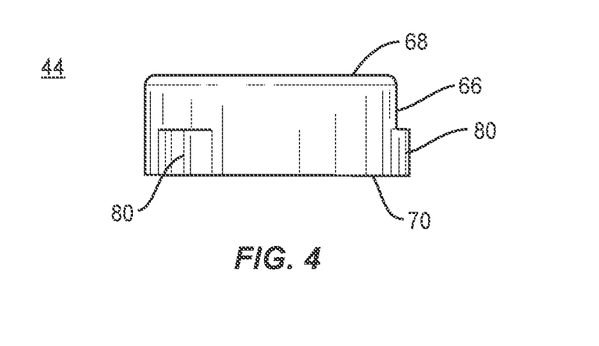
FIG. 4 is a side view of the components shown in FIG. 3.
Figure 5:
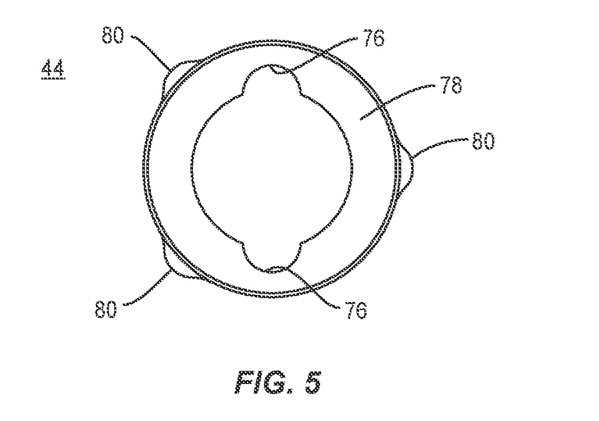
FIG. 5 is a plan view of the components shown in FIG. 3.
Figure 6:
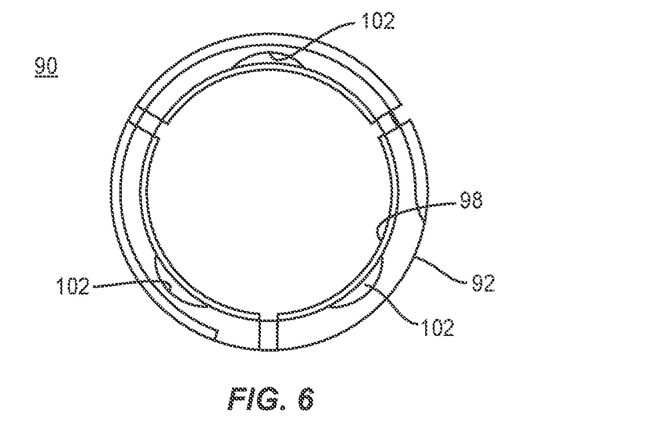
FIG. 6 is a plan view of components of the system shown in FIG.
Figure 7:
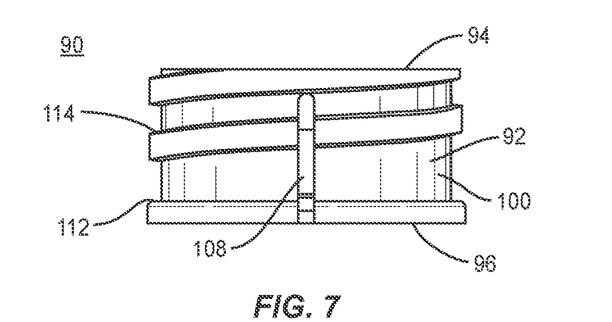
FIG. 7 is a side view of the components shown in FIG. 6.
Figure 8:
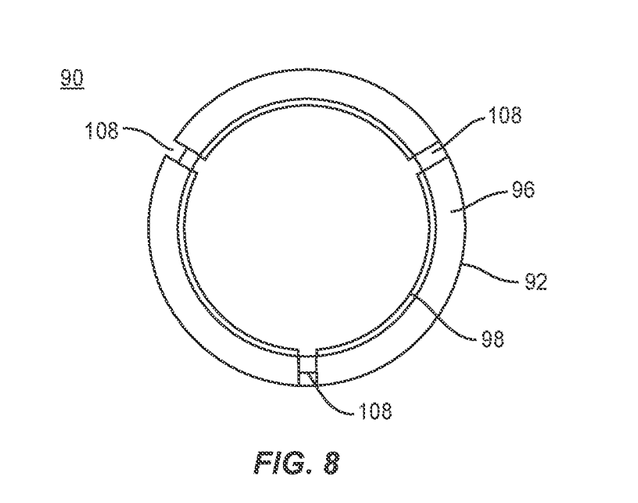
FIG. 8 is a plan view of the components shown in FIG. 6.
Figure 9:
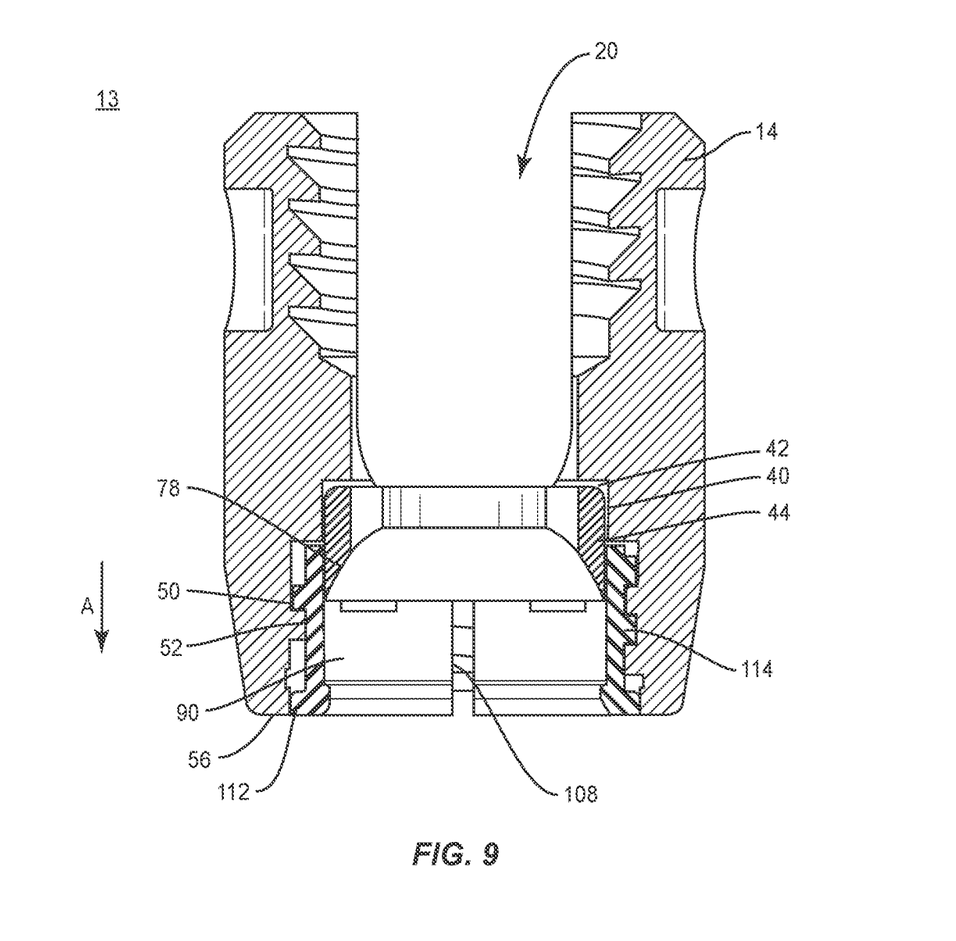
FIGS. 9, 10, 11, 12 are cross section views of components of one embodiment of a spinal implant system illustrating assembly.
Figure 10:
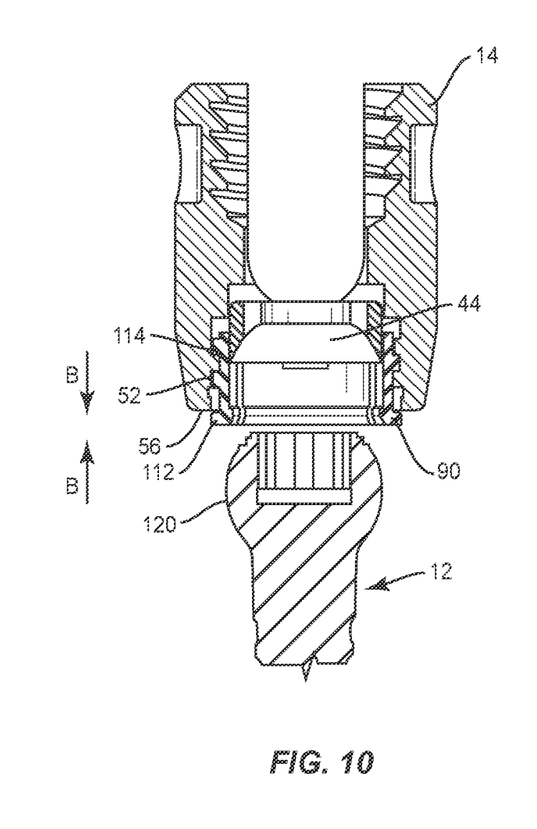
Figure 11:
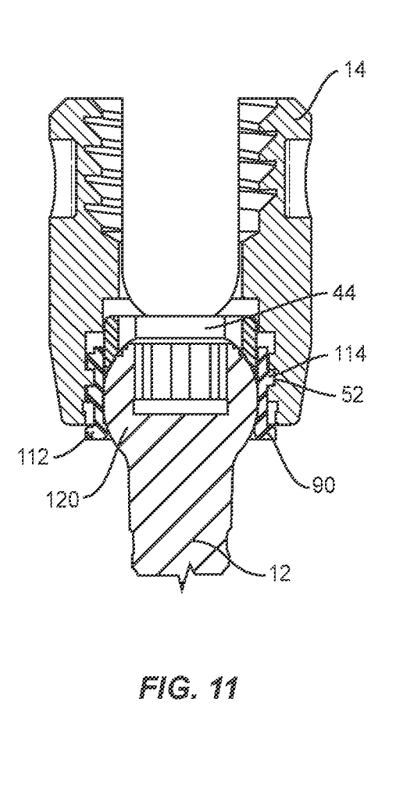
Figure 12:
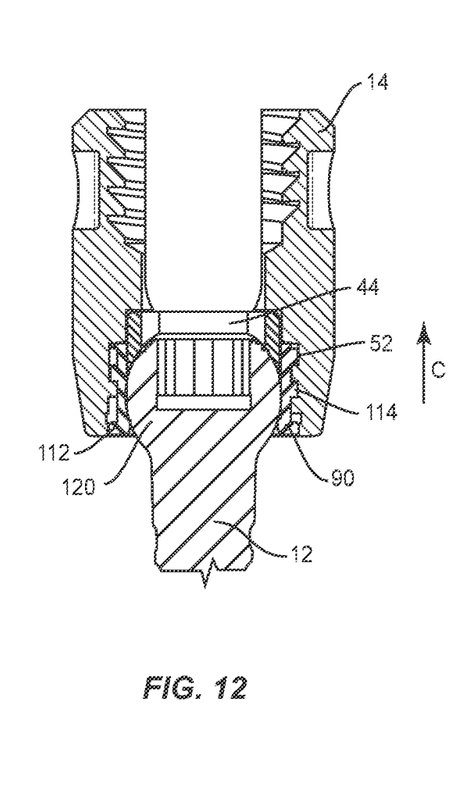

Slots 108 provide flexibility to sleeve 92 such that collet 90 includes an expandable orientation, as shown in FIGS. 10 and 11, and a non-expandable orientation, as shown in FIGS. 9 and 12. For example, screw shaft 12 is engageable with collet 90 such that slots 108 facilitate a snap fit engagement of collet 90 with head 120. As such, sleeve 92 expands upon engagement with head 120 so that head 120 can slide through the opening of surface 94 and the cavity of surface 98, and sleeve 92 contracts or snap fits around head 120 for connection therewith. In some embodiments, surface 98 may be disposed with head 120 in alternate fixation configurations, such as, for example, friction fit, pressure fit, locking protrusion/recess, locking keyway and/or adhesive.

Surface 100 includes a threaded surface 114. In some embodiments, surface 114 may include a single thread turn or a plurality of discrete threads. Surface 114 is configured for a threaded engagement with surface 52 of receiver 14, as described herein. Engagement of surfaces 52, 114 is configured to translate collet 90 axially between a closed position to provisionally fix the components of head assembly 13, an open position for engaging and connecting with screw shaft 12, and a closed position to fix position of collet 90 and/or screw shaft 12 with receiver 14, as described herein. Collet 90 includes a circumferential flange 112.

Screw shaft 12 includes head 120 and a shaft 122. Head 120 includes a tool engaging portion 124 configured to engage a surgical tool or instrument, as described herein. In some embodiments, portion 124 includes a hexagonal cross-section to facilitate engagement with a surgical tool or instrument, as described herein. In some embodiments, portion 124 may have alternative cross-sections, such as, for example, rectangular, polygonal, hexalobe, oval, or irregular. In some embodiments, head 120 includes a surface 126 that defines a plurality of ridges 128 to improve purchase of head 120 with crown 44. In some embodiments, head 120 includes an outer surface. In some embodiments, the outer surface includes planar surfaces, such as, for example, flats and arcuate surfaces. Head 120 is configured for attachment with collet 90 of head assembly 13, as described herein. Shaft 122 is configured to penetrate tissue, such as, for example, bone. In some embodiments, shaft 122 includes an outer surface having an external thread form. In some embodiments, the external thread form may include a single thread turn or a plurality of discrete threads.

Collet 90 is disposable with receiver 14 in a relatively fixed position and a non-expandable orientation to facilitate provisional assembly of the components of head assembly 13, as shown in FIG. 9. Collet 90 is axially translatable with crown 44 and relative to the components of head assembly 13, for example, the inner surface of receiver 14 to dispose collet 90 in an open position and an expandable orientation, as shown in FIGS. 10 and 11, for engaging and connecting with screw shaft 12. Collet 90 is translatable with crown 44 to a closed position and a non-expandable orientation, as shown in FIG. 12, to fix position of collet 90 and/or screw shaft 12 with receiver 14 in an assembly of the components of bone fastener 180.

For example, crown 44 is connected with collet 90 such that flanges 80 are mated with notches 102. Collet 90 is threaded with surface 52 of receiver 14, such that the assembly of collet 90/crown 44 is disposed with cavity 20 in a relatively fixed position, as described herein. The assembly of collet 90/crown 44 can be pre-assembled and/or a surgical driver can engage recesses 76 to rotate collet 90/crown 44 to simultaneously drive and rotate collet 90 relative to receiver 14 to move collet into the closed position, as shown in FIG. 9. In the closed position, collet 90 is releasably locked with receiver 14. The surgical driver engages recesses 76 to rotate collet 90/crown 44, for example, 180 angular degrees in a clockwise direction, to simultaneously drive and rotate collet 90 relative to receiver 14, in the direction shown by arrow A in FIG. 9, for translation to an open position, as shown in FIGS. 10 and 11. Flange 112 extends from an end surface 56 of receiver 14 and collet 90 is expandable, as described herein, to facilitate connection with screw shaft 12.

Screw shaft 12 and head assembly 13 are engaged, in the direction shown by arrows B in FIG. 10, for assembly of the components of bone fastener 180. Sleeve 92 expands upon engagement with head 120 and head 120 slides into the cavity of surface 98. Sleeve 92 contracts around head 120, as shown in FIG. 11, to provide a snap fit assembly of collet 90 and screw shaft 12.

The surgical driver engages recesses 76 and rotates crown 44, for example, 180 angular degrees in a counter-clockwise direction, to simultaneously drive and rotate collet 90. Such rotation of collet 90 threads and translates collet 90 relative to receiver 14 to the closed position, as shown in FIG. 12. Crown 44 engages lip 48. Surface 50 resists and/or prevents expansion of collet 90 such that collet 90 is disposed in a non-expandable orientation with head assembly 13 in the closed position. In the closed position, collet 90 and/or screw shaft 12 are in fixed position with receiver 14 in an assembly of the components of bone fastener 180.

In some embodiments, collet 90 is configured to interface head 120 such that shaft 122 is fixed relative to receiver 14 forming a fixed axis bone fastener. In some embodiments, surface 98 is configured to interface head 120 such that shaft 122 rotatable about multiple axes relative to receiver 14. In some embodiments, shaft 122 is rotatable in one or a plurality of planes relative to receiver 14, similar to that described herein, and/or rotatable about axis X1 in an angular range of 360 degrees. In some embodiments, assembly of screw shaft 12 and head assembly 13 forms a multi-axial bone fastener. In some embodiments, shaft 122 is rotatable in a plane, such as, for example, a sagittal plane relative to receiver 14 forming a sagittal adjusting bone fastener.

In some embodiments, manual engagement and/or non-instrumented assembly of collet 90 and screw shaft 12 includes coupling without use of separate and/or independent instrumentation engaged with screw shaft 12 components to effect a provisional assembly. In some embodiments, manual engagement and/or non-instrumented assembly includes a practitioner, surgeon and/or medical staff grasping collet 90 and screw shaft 12 and forcibly assembling the components. In some embodiments, collet 90 may be previously assembled with receiver 14 and/or crown 44. In some embodiments, manual engagement and/or non-instrumented assembly includes a practitioner, surgeon and/or medical staff grasping collet 90 and screw shaft 12 and forcibly snap fitting the components together, as described herein. In some embodiments, manual engagement and/or non-instrumented assembly includes a practitioner, surgeon and/or medical staff grasping collet 90 and screw shaft 12 and forcibly pop fitting the components together and/or pop fitting collet 90 onto screw shaft 12, as described herein.

In some embodiments, a force in a range of 2-50 N is required to manually engage collet 90 and screw shaft 12 and forcibly assemble the components. For example, a force in a range of 2-50 N is required to snap fit and/or pop fit assemble collet 90 and screw shaft 12. In some embodiments, a force in a range of 5-10 N is required to manually engage collet 90 and screw shaft 12 and forcibly assemble the components. For example, a force in a range of 5-10 N is required to snap fit and/or pop fit assemble collet 90 and screw shaft 12. In some embodiments, screw shaft 12 is manually engaged with collet 90 in a non-instrumented assembly, as described herein, such that removal of collet 90 and screw shaft 12 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

In some embodiments, spinal implant system 10 comprises a spinal implant kit, as described herein, which includes a plurality of screw shafts 12, crowns 44, collets 90 and receivers 14 to comprise a selected bone fastener configuration and/or selected movement, as described herein. In some embodiments, the components of spinal implant system 10 are interchangeable.

In assembly, operation and use, spinal implant system 10, similar to the systems and methods described herein, includes a screw shaft 12 for connection with a head assembly 13, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, spinal implant system 10 includes a screw shaft 12 for connection with a head assembly 13 forming bone fastener 180 having a selected movement, as described herein. Bone fastener 180 and one or a plurality of spinal implants, such as, for example, spinal rods can be delivered or implanted as a pre-assembled device or can be assembled in situ. The components of spinal implant system 10 may be may be completely or partially revised, removed or replaced. In some embodiments, a screw shaft 12 is interchangeable with head assembly 13 to comprise a bone fastener 180 having a selected movement, such as, for example, multi-axial movement, sagittal angulation movement, fixed axis movement, mono-axial movement and/or uni-planar movement.

For example, a crown 44 and a collet 90 are mated to comprise a selected bone fastener configuration and/or movement with a receiver 14. A pre-assembly of collet 90/crown 44 is disposed with cavity 20 in a relatively fixed position and a non-expandable orientation to facilitate provisional assembly of the components of head assembly 13, as shown in FIG. 9. A surgical driver rotates collet 90/crown 44, for example, in a clockwise direction, relative to receiver 14 to axially translate collet 90 to an open position, as shown in FIG. 10. Screw shaft 12 and head assembly 13 are engaged, in the direction shown by arrows B in FIG. 10, for assembly of the components of bone fastener 180. Sleeve 92 expands upon engagement with head 120 and head 120 slides into the cavity of surface 98. Sleeve 92 contracts around head 120, as shown in FIG. 11, to provide a snap fit assembly of collet 90 and screw shaft 12.

The surgical driver simultaneously drives and rotates collet 90/crown 44, for example, in a counter-clockwise direction relative to receiver 14. Such rotation of collet 90 threads and translates collet 90, in the direction shown by arrow C in FIG. 12, for translation relative to receiver 14 to the closed position, as shown in FIG. 12, Surface 50 resists and/or prevents expansion of collet 90 such that collet 90 is disposed in a non-expandable orientation with head assembly 13 in the closed position. In the closed position, collet 90 and/or screw shaft 12 are in fixed position with receiver 14 in an assembly of the components of bone fastener 180.

In use, for treatment of a spinal disorder, bone fastener 180 including assembled screw shaft 12 and head assembly 13 can be threaded and engaged with tissue. In some embodiments, the selected bone fastener 180 is disposed adjacent vertebrae at a surgical site and is manipulated to drive, torque, insert or otherwise connect shaft 122 with vertebrae in connection with a surgical procedure, as described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 180 such as those described herein and/or fixation elements, which may be employed with a single vertebral level or a plurality of vertebral levels. In some embodiments, bone fasteners 180 may be engaged with vertebrae in various orientations, such as, for example, series, parallel, offset, staggered and/or alternate vertebral levels. In some embodiments, bone fasteners 180 may be configured as multi-axial screws, sagittal angulation screws, pedicle screws, mono-axial screws, uni-planar screws, fixed screws, anchors, tissue penetrating screws, conventional screws and/or expanding screws. In some embodiments, bone fasteners 180 may be employed with wedges, anchors, buttons, clips, snaps, friction fittings, compressive fittings, expanding rivets, staples, nails, adhesives, connectors, fixation plates and/or posts.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of assembly for a bone fastener, the method comprising the steps of:
   connecting a collet with a crown and disposing the collet with an inner surface of an implant receiver such that the collet is threaded with the inner surface;
   disposing the collet in a relatively fixed position with the implant receiver and a non-expandable orientation;
   translating the collet relative to the implant receiver to an expandable orientation; and
   manually engaging a screw shaft with the collet to connect the implant receiver with the screw shaft.

2. A method as recited in claim 1, further comprising translating the collet relative to the implant receiver to a non-expandable orientation to comprise a bone fastener.

3. A method as recited in claim 1, wherein the collet is simultaneously rotatable with the crown.

4. A method as recited in claim 1, wherein the screw shaft is manually engaged with the collet in a non-instrumented assembly of the screw shaft and the collet to connect the implant receiver with the screw shaft.

5. A method as recited in claim 1, wherein the collet comprises a circumferential sleeve, the sleeve defining spaced apart slots, the slots each extending through a wall of the sleeve.

6. A method as recited in claim 1, wherein the collet comprises a circumferential sleeve, the sleeve defining three spaced apart slots, the slots each extending through a wall of the sleeve.

7. A method as recited in claim 1, wherein the collet is translatable relative to the implant receiver between the expandable orientation and the non-expandable orientation such that the screw shaft is fixed with the implant receiver.

8. A method as recited in claim 1, wherein the crown includes spaced apart circumferential outer flanges, the outer flanges engaging the collet as the collet translates relative to the implant receiver.

9. A method as recited in claim 1, wherein the crown includes at least one mating element that is configured to interface with a surgical instrument for rotation of the crown.

10. A method as recited in claim 1, wherein the collet is configured to be translated by engaging the crown with a surgical instrument prior and translating the surgical instrument.

11. A method of assembly for a bone fastener, the method comprising the steps of:
    releasably locking a collet with an inner surface of an implant receiver in a closed position, the collet being threaded with the inner surface;
    translating the collet relative to the implant receiver to an open position; and
    manually engaging a screw shaft with the collet to connect the implant receiver with the screw shaft.

12. A method as recited in claim 11, further comprising the step of translating the collet with the screw shaft relative to the implant receiver to a closed position in a non-expandable orientation to comprise a bone fastener.

13. A method as recited in claim 11, wherein the collet is connected with a crown disposed with the implant receiver.

14. A method as recited in claim 11, wherein the screw shaft is manually engaged with the collet in a non-instrumented assembly of the screw shaft and the collet to connect the implant receiver with the screw shaft.

15. A method as recited in claim 11, wherein the collet comprises a circumferential sleeve, the sleeve defining spaced apart slots, the slots each extending through a wall of the sleeve.

16. A method as recited in claim 11, wherein the collet comprises a circumferential sleeve, the sleeve defining three spaced apart slots, the slots each extending through a wall of the sleeve.

17. A method as recited in claim 11, wherein the collet is translatable relative to the implant receiver between an expandable orientation and a non-expandable orientation such that the screw shaft is fixed with the implant receiver.

18. A method as recited in claim 11, further comprising connecting the collet with a crown before translating the collet relative to the implant receiver.

19. A method as recited in claim 18, wherein the crown includes spaced apart circumferential outer flanges, the outer flanges engaging the collet as the collet translates relative to the implant receiver.

20. A method of assembly for a bone fastener, the method comprising the steps of:

connecting a collet with a crown and disposing the collet with an inner surface of an implant receiver such that the collet is threaded with the inner surface, the collet comprising a circumferential sleeve, the sleeve defining spaced apart slots, the slots each extending through a wall of the sleeve;

disposing the collet in a relatively fixed position with the implant receiver and a non-expandable orientation;

translating the collet relative to the implant receiver to an expandable orientation, the crown including spaced apart circumferential outer flanges, the outer flanges engaging the collet as the collet translates relative to the implant receiver; and manually engaging a screw shaft with the collet to connect the implant receiver with the screw shaft.

* * * * *